United States Patent [19]

Matthewson

[11] 4,341,760
[45] Jul. 27, 1982

[54] SYNERGISTIC COMPOSITIONS

[75] Inventor: Michael D. Matthewson, Berkhamsted, England

[73] Assignee: Burroughs Wellcome Co., Research Triangle Park, N.C.

[21] Appl. No.: 863,737

[22] Filed: Dec. 23, 1977

[30] Foreign Application Priority Data

Dec. 24, 1976 [GB] United Kingdom ............... 54049/76
Apr. 7, 1977 [GB] United Kingdom ............... 14770/77

[51] Int. Cl.³ ..................... A01N 37/00; A01N 37/34; A01N 57/00; A61L 9/04
[52] U.S. Cl. ..................... 424/45; 424/198; 424/200; 424/203; 424/205; 424/211; 424/212; 424/213; 424/216; 424/219; 424/225; 424/304; 424/305
[58] Field of Search ............... 424/304, 203, 45, 198, 424/200, 205, 211, 212, 213, 216, 219, 225

[56] References Cited

U.S. PATENT DOCUMENTS 2,725,328 11/1955 Diveley et al. ................ 424/173
3,993,774 11/1976 Searle et al. ................ 424/304 X
4,031,239 6/1977 Schrider et al. ............... 424/304 X

FOREIGN PATENT DOCUMENTS 1448228 6/1974 United Kingdom .

OTHER PUBLICATIONS

Chemical Week, Apr. 12, 1969, p. 62.

Primary Examiner—Allen J. Robinson
Attorney, Agent, or Firm—Donald Brown

[57] ABSTRACT

Acaricidal compositions comprising a pyrethroid of formula

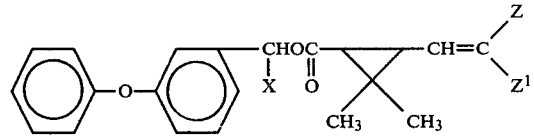

wherein Z and $Z^1$ are the same or different and each is halo and wherein X is hydrogen or cyano, provided that when Z and $Z^1$ are both chloro, X must be cyano together with at least one organophosphorus compound, formulations containing them and their use for the control of veterinary ectoparasites of the sub-Orders Ixodoidea and Sarcoptiformes.

17 Claims, No Drawings

SYNERGISTIC COMPOSITIONS

This invention relates to novel pesticidal compositions, their preparation, formulations containing them, for preparation of such formulations and to their use for the control of pests of the sub-Orders Ixodoidea and Sarcoptiformes.

Pyrethroids embraced by formula (I):

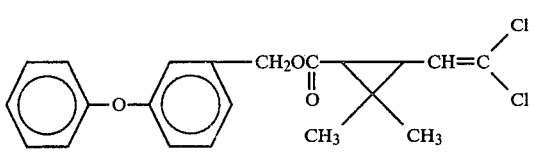

are known from U.K. Pat. No. 1,413,491 to possess insecticidal activity, and are known from South African Pat. No. 3211/1975 to possess acaricidal activity.

Pests of the Class Insecta and of the Order Acarina are troublesome to man, animal and plants. They are vectors of disease, and economic losses result from their depredations on plants and animals. Control of such pests over the years has come to depend strongly upon the use of chemical pesticides which can be naturally occuring compounds or synthetic organic chemicals.

Organophosphorus pesticides are used in both the agricultural and veterinary fields with varying degrees of success. Some of these substances are common to both fields such as diazinon and malathion whilst others have been solely employed in the agricultural field, for example fenitrothion. In recent years resistance to organophosphorus compounds has evolved in certain strains of Insects and Acarids both of agricultural and veterinary importance and accordingly the need for new, effective insecticides and acaricides has arisen.

It is known from Japanese Patent Publication No. 058-237/1975, that potentiation of activity occurs between a pyrethroid of formula (I) and certain organophosphorus compounds against Insects and certain Mites of agricultural importance. Employing such potentiating compositions, renders the use of pyrethroids of formula (I) more economic. The Japanese publication also suggests that the potentiation is due to the interaction between the inhibition of the enzyme acetylcholinesterase by the organophosphorus compound at the ganglionic junctions of the pest, which results in ganglionic nerve paralysis, and the disturbance of axonal nerve transmittance through the cell membranes of the nerve axons of the pest by the pyrethroid, which results in impaired axonal nerve transmission.

It has now been surprisingly found that there is potentiation between a pyrethroid of formula (II) and certain organophosphorus compound against pests of veterinary importance which are resistant to conventional organophosphorus compounds and which belong to the sub-Orders Ixodoidea and Sarcoptiformes. It is believed that the potentiation is due to the inhibition by the organophosphorus compound of certain esterases which degrade pyrethroids. The various rates at which different groups of arthropod pests, even within the same Order of classification, metabolise a pyrethroid makes it difficult to predict potentiation in one group of arthropod pests from a knowledge of potentiation in another group. This unpredictability is demonstrated by the absence of potentiation of insecticidal activity between a compound of formula (I) and an organophosphorus compound in respect of Insects of veterinary importance. (See Tables 6 to 9 below).

The pyrethroid for use in the present invention is selected from the esters of formula (II) below:

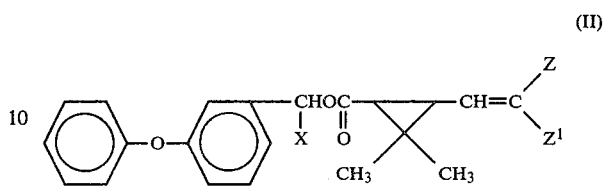

wherein $Z^1$ and $Z$ may be the same or different and each is halo such as chloro, bromo or fluoro; and X is hydrogen or cyano; provided that when both of $Z^1$ and $Z$ are chloro X must be cyano.

Formula (II) is intended to encompass all the geometric and optical isomers. More particularly the acid moiety of the esters may be selected from the (+)-cis-isomer, the (+)-trans-isomer, the (±)-cis-isomer, the (±)-trans-isomer and the (±)-cis-trans-isomer; the stereochemistry referring to that of the cyclopropane ring. Moreover, when X is cyano the alcohol moiety of the ester may be selected from the (+)-isomer, the (−)-isomer or the (±)-isomer.

Particularly useful esters are those wherein Z is selected from chloro and bromo. The preferred pyrethroid of this invention is: (−)-α-Cyano-3-phenoxybenzyl-(+)-cis-2,2-dimethyl-3-(2,2-dibromovinyl)cyclopropane-1-carboxylate (decamethrin)

The esters of formula (II) may be used in combination with phosphate and phosphorothioate compounds possessing intrinsic acaricidal activity. The organophosphorus compounds found to be effective are:

O,O-diethyl-O-(3-chloro-4-methyl-7-coumarinyl)phosphorothioate (coumaphos);

O,O-diethyl-O-(2,5-dichloro-4-bromophenyl) phosphorothioate (bromophos-Ethyl);

O,O-diethyl-O-(2-isopropyl-6-methyl-pyrimidin-4-yl)phosphorothioate (diazinon);

2,3-p-dioxanedithiol S,S-bis, O,O-diethyl phosphorodithioate (dioxathion);

O,O-diethyl-O-(3,5,6-trichloro-2-pyridyl) phosphorothioate (chlorpyrifos);

O,O,O',O'-tetraethyl, S,S'-methylenediphosphorodithioate (ethion);

3-(Dimethoxyphosphinyloxy)-N-dimethyl-cis-crotonamide (dicrotophos);

S-(1,2-dicarbethoxy ethyl)-O,O-dimethylphosphorodithioate (malathion);

cis-1-methyl-2-(1-phenylethoxycarbonyl)vinylphosphate(crotoxyphos);

O-ethyl-O-(quinol-8-yl)phenylphosphorothioate(oxinothiophos);

(S-{5,7-dichlorobenzoxazol-2-yl-methyl}-O,O-diethyl phosphorodithioate)(benoxaphos);

S-[{(4-chlorophenyl)-thio]methyl}-O,O-diethyl phosphorodithioate(carbophenothion);

S-{(1,3-dihydro-1,3-dioxo-2H-isoindol-2-yl)-methyl}-O,O-dimethylphosphorodithioate(phosmet);

2-Chloro-1-(2,4-dichlorophenyl)vinyldiethylphosphate(chlorfenvinphos)

and a 1:1 weight by weight mixture of chlorfenvinphos and dioxathion.

Particularly high potentiation is achieved with combinations containing coumaphos, chlorfenvinphos, diazinon, ethion and the mixture of dioxathion and chlorfenvinphos.

The potentiating compositions of this invention are highly effective against strains of acarines which are susceptible to conventional organophosphorus acaricides as well as to those strains which are resistant to conventional organophosphorus acaricides such as *Boophilus microplus* (Can.) and *B. decoloratus* (Koch) and in addition those strains resistant to pyrethroids. The compositions of this invention may therefore be used to control acarine ectoparasites of animals, particularly those ticks of the genera Boophilus, Rhipicephalus, Amblyomma, Hyalomma, Ixodes, Haemaphysalis, Dermacentor, and Anocentor, and mites of veterinary importance for example the sheep scab mite *Psoroptes ovis*, and other ectoparasites of the sub-Orders Ixodoidea and Sarcoptiformes. Such ectoparasites infest stock and domestic animals and fowls, depending upon the location of the host and the particular ectoparasite. Common hosts are cattle, pigs, sheep, goats, horses, camels, chickens, dogs and cats.

The compositions of this invention may be used for protecting the host against infestations of Ixodid and Sarcoptic pests by application of the compositions themselves or in a diluted form in known fashion, as a dip, a spray, a dust, a paste, cream, gel, foam, shampoo or grease, a pressure-pack, an impregnated article, or a pour-on formulation. Dips are not applied per se, but the animals are immersed in a dipping bath containing the dip wash. Sprays may be applied by hand or by means of a spray race or arch or automatic treadle. Dusts may be distributed over the animals by means of a powder gun by hand application from suitable containers or incorporated in perforated bags attached to trees or rubbing bars. Pastes, foams, creams, gels, shampoos and greases may be applied manually or distributed over the surface of an inert material against which animals rub and transfer the material to their skins. Pour-on formulations are dispensed as a unit of liquid or small volume on to the backs of animals such that all or most of the liquid is retained on the animals.

The compositions may be presented either as formulations ready for use on the animals or as formulations requiring further dilution prior to application, but both types of formulations comprise a pyrethroid as defined above in combination with at least one organophosphorus compound as defined above in intimate admixture with one or more carriers or diluents. The carriers may be gaseous or solid or liquid or comprise mixtures of such substances and may be selected from one or more of the following: a solvent, an inert carrier, wetting, stabilising, emulsifying, thickening, dispersing and surface active agents.

Dusts may be prepared by intimate admixture of the chosen compound with a powdered solid inert carrier for example suitable clays, kaolin, talcs, powdered chalk, calcium carbonate, Fuller's Earth, gypsum, diatomaceous earths and vegetable carriers.

Sprays of a composition of this invention may comprise a solution in an organic solvent (e.g. those listed below) or an emulsion in water (dip wash or spray wash) prepared in the field from an emulsifiable concentrate (otherwise known as a water miscible oil) or a water dispersible powder which may also be used for dipping purposes. The concentrate preferably comprises a mixture of the active ingredients, with or without an organic solvent and one or more emulsifiers. Solvents may be selected from kerosene, ketones, alkanols, xylene, aromatic naphtha, and other solvents known in the formulating art. The concentration of emulsifiers may be varied within wide limits and are conveniently non-ionic or a mixture of non-ionic and anionic surfactants. The non-ionic surfactants will include polyoxyalkylene ethers of alkyl phenols, or of alcohols. The anionic compounds include salts of alkylaryl sulphonic acids.

Dip washes may be prepared not only from emulsifiable concentrates but also from wettable powders comprising a composition of this invention in intimate admixture with an inert carrier and one or more surface active agents, and possibly a stabiliser and/or an antioxidant.

Greases may be prepared from vegetable oils, synthetic esters of fatty acids or wool fat together with an inert base such as soft paraffin. A composition of this invention is preferably distributed uniformly through the mixture in solution or suspension. Greases may also be made from emulsifiable concentrates by diluting them with an ointment base.

Pastes are also semi-solid preparations in which a composition of this invention may be present as an uniform dispersion in a suitable base such as soft or liquid paraffin or made on a non-greasy basis with glycerin, mucilage or a suitable soap. As greases and pastes are usually applied without further dilution they should contain the appropriate percentage of the composition required for treatment.

Aerosol sprays may be prepared as a simple solution of the active ingredients in the aerosol propellant and a co-solvent such as halogenated alkanes and the solvents referred to above, respectively. Pour-on formulations may be made as a solution emulsion or suspension of a composition of this invention in a liquid medium which is of a viscosity such as to minimize loss of the formulation by run off from the surface of the animals. The pour-on formulation may be applied by a drenching gun, syringe or ladle or any other method known in the art.

A composition of the present invention preferably contains (5–95%) of a defined pyrethroid for example one selected from structural formula (II) and between (5–95%) of an organo-phosphorus compound defined hereinabove. The concentration of a composition applied to the pests or to their environment may be in the range of (0.0001–20%).

It will be appreciated from the foregoing that what we will claim may comprise any novel feature described herein, principally and not exclusively, for example:
 (a) A novel composition comprising an ester of formula (II) in combination with at least one organophosphorus compound;
 (b) A pesticidal formulation comprising a composition as defined in paragraph (a) together with a carrier therefor;
 (c) A method of producing such a formulation; and
 (d) A method of controlling verterinary octoparasites of the sub-Orders Ixodoidea and Sarcoptiformes comprising the application to the ectoparasite or its environment, a composition or formulation as defined in paragraph (a) or (b).

The following Examples are provided by way of an illustration of the present invention and should not be construed as in any way constituting a limitation thereof.

EXAMPLE 1

Engorged female ticks of the Biarra strain of *Boophilus microplus* are immersed, in groups of 20 ticks per concentration, in a range of dilutions of the organophosphorus compound in combination with (−)-β-cyano-3-phenoxybenzyl-(+)-cis-2,2-dimethyl-3-(2,2-dibromovinyl)cyclopropane-1-carboxylate (hereinafter referred to as Decamethrin) at different ratios or organophosphorus compound to Decamethrin.

The composite wash is prepared immediately prior to the test by dilution (with water) of the two constituents. The constituents may be in the form of miscible oil or wettable powder formulations. The desired range of concentrations for the test is obtained by further dilution of this master solution or wash.

The ticks are removed from the wash after 10 minutes; dried, and stuck dorsal side down on double-sided adhesive tape. They remain in this position for 14 days when the numbers laying viable eggs are determined. From this data a regression line is plotted (concentration against % inhibition of egg-production) and the IR90 and IR99 values determined (Table 1).

IR90 = concentration at which 90% inhibition of egg-production occurs.

IR99 = concentration at which 99% inhibition of egg-production occurs.

The values so obtained for the composite wash are compared with similar values obtained for the constituents of the composite wash when used alone. By reference to the equation for the harmonic mean, the factor of potentiation is determined (Table 2).

The equation for the harmonic mean is:

$$X = \frac{\text{Proportion of } A + \text{Proportion of } B}{\frac{\text{Proportion of } A}{IR90\ A} + \frac{\text{Proportion of } B}{IR90\ B}}$$

$$Y = \frac{X}{IR90 \text{ mixture of } A \text{ and } B}$$

$$\text{Factor of Potentiation } (FOP) = \frac{Y \times \text{Proportion of } A}{\text{Proportion of } A + B}$$

The FOP figures for the IR99 values were calculated in the same way.

TABLE 1

IR/90/99 Values for the Ixodicides and Decamethrin alone and composites of these at various ratios

| DECAMETHRIN COMPOSITE WITH | IXODICIDE ALONE | | RATIO 1:1 | | RATIO 5:1 | | RATIO 10:1 | | RATIO 20:1 | |
|---|---|---|---|---|---|---|---|---|---|---|
| | IR90 | IR99 | IR90 | IR99 | IR90 | IR99 | IR90 | IR99 | IR90 | IR99 |
| BROMOPHOS ETHYL | 0.18 | 0.38 | 0.00050 | 0.00098 | 0.0017 | 0.0029 | | | | |
| DIOXATHION | >1.0 | — | 0.00070 | 0.0017 | 0.0020 | 0.0031 | | | | |
| CHLORPYRIFOS | 0.085 | 0.24 | 0.00056 | 0.00010 | 0.00016 | 0.0032 | | | | |
| ETHION | 0.14 | 0.23 | 0.00032 | 0.00058 | 0.00010 | 0.00017 | | | | |
| CHLORFENVINPHOS | 0.15 | 0.42 | 0.00017 | 0.00032 | 0.0012 | 0.0028 | 0.0018 | 0.0028 | 0.0027 | 0.0045 |
| DECAMETHRIN | 0.0019 | 0.0039 | | | | | | | | |

Key:- Ratio Ixodicide/Decamethrin

TABLE 2

Factors of Potentiation of composites of certain Ixodicides and Decamethrin

| DECAMETHRIN COMPOSITE WITH | RATIO 1:1 | | RATIO 5:1 | | RATIO 10:1 | | RATIO 20:1 | |
|---|---|---|---|---|---|---|---|---|
| | IR90 | IR99 | IR90 | IR99 | IR90 | IR99 | IR90 | IR99 |
| BROMOPHOS ETHYL | 3.8 | 3.9 | 5.4 | 6.3 | | | | |
| DIOXATHION | >2.7 | — | >1.6 | — | | | | |
| CHLORPYRIFOS | 3.3 | 3.9 | 5.3 | 5.8 | | | | |
| ETHION | 5.8 | 6.6 | 9.2 | 10.8 | | | | |
| CHLORFENVINPHOS | 11.2 | 12.0 | 7.7 | 6.6 | 9.6 | 12.6 | 11.3 | 15.2 |

Key: -Ratio Ixodicide/Decamethrin

EXAMPLE 3

Miscible-Oil Formulations

| | 20:1 | 1:1 | 1:20 | |
|---|---|---|---|---|
| Dioxathion | 20.0 | 10.5 | 1.0 | pts. by wt. |
| Decamethrin | 1.0 | 10.5 | 20.0 | pts. by wt. |
| Esso Solvent 200 | 59.0 | 54.0 | 49.0 | pts. by wt. |
| Ethylan KEO | 20.0 | 20.0 | 20.0 | pts. by wt. |
| Cyclohexanone | — | 5.0 | 10.0 | pts. by wt. |
| | 100.0 | 100.0 | 100.0 | |

Ethylan KEO is an emulsifying agent which is a nonyl phenol ethoxylate condensate with an ethylene oxide average chain length of 9.5 mols, supplied by Lankro Chemicals Ltd.

Esso Solvent 200 is a mobile oil which consists of 95% of aromatic hydrocarbons.

EXAMPLE 4

Dusting Powder Formulations

| | 20:1 | 1:1 | 1:20 | |
|---|---|---|---|---|
| Coumaphos | 0.01 | 0.10 | 0.20 | pts. by wt. |
| Decamethrin | 0.20 | 0.10 | 0.01 | pts. by wt. |
| Talc | 99.79 | 99.8 | 99.79 | pts. by wt. |
| | 100.0 | 100.0 | 100.0 | |

EXAMPLE 5

Wettable Powder Formulations

|  | w/w | w/w | w/w |
|---|---|---|---|
| Coumaphos | 1.0% | 15.0% | 40.0% |
| Decamethrin | 20.0 | 15.0 | 2.0 |
| Diatomaceous Earth | 76.5 | 50.0 | — |
| Kaolin | — | 17.5 | 54.0 |
| Dispersing Agent | 2.0 | 2.0 | 3.0 |
| Wetting Agent | 0.5 | 0.5 | 1.0 |
|  | 100.0 | 100.0 | 100.0 |

|  | w/w | w/w |
|---|---|---|
| Ethion | 2.0 | 25.0 |
| Decamethrin | 20.0 | 1.5 |
| Diatomaceous Earth | 60.5 | 36.0 |
| Fullers Earth | 15.0 | 35.0 |
| Dispersing Agent | 2.0 | 2.0 |
| Wetting Agent | 0.5 | 0.5 |
|  | 100.0 | 100.0 |

EXAMPLE 6

Pressure-Pack Formulations

In the following examples one of three pesticide mixtures may be used:

| Mixture 1 | Dioxathion | 10 parts by weight |
|---|---|---|
|  | Chlorfenvinphos | 10 parts by weight |
|  | Decamethrin | 1 part by weight |
| Mixture 2 | Dioxathion | 0.5 parts by weight |
|  | Chlorfenvinphos | 0.5 parts by weight |
|  | Decamethrin | 1 part by weight |
| Mixture 3 | Dioxathion | 0.5 parts by weight |
|  | Chlorfenvinphos | 0.5 parts by weight |
|  | Decamethrin | 20 parts by weight |

The above pesticide mixtures may be employed to formulate pressure packs containing between 0.0001% w/w and 20% w/w of each pesticide mixture as illustrated by the following examples:

EXAMPLE 7

| Pesticide mixture (either No. 1, 2 or 3 above) | 0.0001% w/w |
|---|---|
| Odourless kerosene | 10.0000% w/w |
| Methyl chloroform | 29.9999% w/w |
| 50/50 mixture of trichlorofluoromethane and dichlorodifluoromethane | 60.0000% w/w |
|  | 100.0000% w/w |

EXAMPLE 8

| Pesticide mixture (either No. 1, 2 or 3 above) | 20% w/w |
|---|---|
| Methyl chloroform | 50% w/w |
| Dichlorodifluoromethane | 30% w/w |
|  | 100% w/w |

EXAMPLE 9

Aqueous Suspension Formulations

|  | % w/w | | |
|---|---|---|---|
|  | (a) | (b) | (c) |
| Decamethrin | 1.0 | 8.0 | 20.0 |
| Coumaphos | 20.0 | 8.0 | 1.0 |
| Sodium Dioctyl Sulphosuccinate | 0.2 | 0.2 | 0.2 |
| Xanthan Gum | 0.3 | 0.4 | 0.3 |
| Water | 78.5 | 83.4 | 78.5 |
|  | 100.0 | 100.0 | 100.0 |

EXAMPLE 10

Diluent Free Formulations

|  | % w/w | | |
|---|---|---|---|
|  | (a) | (b) | (c) |
|  | 3.5 | 38.0 | 72.0 |
| Diazinon | 70.0 | 38.0 | 3.6 |
| Epichlorhydrin | 7.0 | 4.0 | 0.4 |
| Ethylan KEO | 19.5 | 20.0 | 24.0 |
|  | 100.0 | 100.0 | 100.0 |

Ethylan KEO is an emulsifying agent which is a nonyl phenol ethoxylate condensate with an ethylene oxide average chain length of 9.5 mols, supplied by Lankro Chemicals Ltd.

REFERENCE EXAMPLE A

Mixtures of permethrin in combination with various organophosphorus compounds were prepared at 1:1, 1:10 and 1:25 ratios (ratio permethrin to organophosphorus compound). Solutions of the pesticides alone were similarly prepared.

The individual pesticides and the mixtures were diluted appropriately and applied by means of a microsyringe to the dorsal thorax of female CTB or Piggery II strain musca domestica flies. This topical application technique was performed on twenty females flies for each concentration of each mixture. The flies were then placed in a cardboard carton with access to sugar water for one day in order to assess mortality. Each concentration of each mixture was tested five times in a linked sequence over a period of several weeks.

The LC50 and LC95 value of each mixture was determined by means of probit analysis. A theoretical LC50 and LC95 value was calculated for each mixture by means of the equation of the harmonic mean.

The theoretical and experimental values were then compared in order to give factors of potentiation values.

The results are given in Tables 3 to 6, which indicate that little or no potentiation was observed.

TABLE 3

LC50 values of individual organophosphorus insecticides and compositions of these with permethrin obtained both theoretically and by experiment against *Musca domestica* (CTB strain) (ratio 1:1)

| Compound | Experimental LC50 Alone ($\mu g/♀$) | Experimental LC50 Mixture as permethrin ($\mu g/♀$) | Calculated LC50 Total ($\mu g/♀$) | Calculated LC50 Mixture as permethrin ($\mu g/♀$) | Factor of Potentiation |
|---|---|---|---|---|---|
| Permethrin | 0.027 | — | — | — | — |
| Bromophos ethyl | 0.102 | 0.029 | 0.043 | 0.021 | 0.74 |
| Chlorpyrifos | 0.094 | 0.025 | 0.042 | 0.021 | 0.84 |
| Bromophos | 0.114 | 0.021 | 0.043 | 0.022 | 1.02 |
| Malathion | 1.349 | 0.036 | 0.053 | 0.026 | 0.73 |
| Diazinon | 0.041 | 0.025 | 0.032 | 0.016 | 0.66 |

LC50 is the minimum lethal dose expressed in $\mu g$ required to kill 50% of the flies

TABLE 4

LC95 values of individual organosphosphorus insecticides and compositions of these with permethrin obtained both theoretically and by experiment against *Musca domestica* (CTB strain) (ratio 1:1)

| Compound | Experimental LC95 Alone ($\mu g/♀$) | Experimental LC95 Mixture as permethrin ($\mu g/♀$) | Calculated LC95 Total ($\mu g/♀$) | Calculated LC95 Mixture as permethrin ($\mu g/♀$) | Factor of Potentiation |
|---|---|---|---|---|---|
| Permethrin | 0.054 | — | — | — | — |
| Bromophos ethyl | 0.170 | 0.097 | 0.082 | 0.041 | 0.43 |
| Chlorpyrifos | 0.161 | 0.083 | 0.081 | 0.041 | 0.49 |
| Bromophos | 0.241 | 0.063 | 0.088 | 0.044 | 0.70 |
| Malathion | 3.671 | 0.105 | 0.107 | 0.053 | 0.51 |
| Diazinon | 0.160 | 0.066 | 0.081 | 0.040 | 0.61 |

LC95 is the minimum lethal dose expressed in $\mu g$ required to kill 95% of the flies

TABLE 5

LD50 values for individual organophosphorus insecticides and compositions of these with permethrin at various ratios against *Musca domestica* (Piggery II strain)

| Compound | LD50 ($\mu g/♀$) | Ratio 1:1 Calculated | Ratio 1:1 observed | Ratio 1:1 Calculated observed | Ratio 1:10 (permethrin/OP) Calculated | Ratio 1:10 observed | Ratio 1:10 Calculated observed | Ratio 1:25 (permethrin/OP) Calculated | Ratio 1:25 observed | Ratio 1:25 Calculated observed |
|---|---|---|---|---|---|---|---|---|---|---|
| Permethrin | 0.235 | — | — | — | — | — | — | — | — | — |
| Dimethoate | 0.179 | 0.20 | 0.20 | 1.0 | 0.18 | 0.13 | 1.4 | — | — | — |
| Diazinon | 2.075 | 0.41 | 0.35 | 1.2 | 1.2 | 0.89 | 1.4 | — | — | — |
| Malathion | 41.70 | 0.46 | 0.42 | 1.1 | 2.45 | 2.49 | 1.0 | 5.36 | 3.0 | 1.8 |
| Chlorpyrifos | 2.171 | 0.41 | 0.38 | 1.1 | 1.25 | 0.76 | 1.7 | — | — | — |
| Bromophos ethyl | 2.663 | 0.42 | 0.39 | 1.1 | 1.38 | 0.50 | 2.8 | — | — | — |
| Pirimiphos methyl | 5.130 | 0.44 | 0.38 | 1.2 | 1.78 | 1.22 | 1.5 | 2.85 | 1.77 | 1.6 |

LD50 is the minimum lethal dose expressed in $\mu g$ required to kill 50% of the flies
OP = organophosphorus compound
Factor of potentiation = $\frac{\text{calculated value}}{\text{observed value}}$

TABLE 6

LD95 values for individual organophosphorus insecticides and compositions of these with permethrin at various ratios against *Musca domestica* (Piggery II strain)

| Compound | LD50 ($\mu g/♀$) | Ratio 1:1 Calculated | Ratio 1:1 observed | Ratio 1:1 Calculated observed | Ratio 1:10 (permethrin/OP) Calculated | Ratio 1:10 observed | Ratio 1:10 Calculated observed | Ratio 1:25 (permethrin/OP) Calculated | Ratio 1:25 observed | Ratio 1:25 Calculated observed |
|---|---|---|---|---|---|---|---|---|---|---|
| Permethrin | 0.63 | — | — | — | — | — | — | — | — | — |
| Dimethoate | 0.66 | 0.65 | 0.53 | 1.2 | 0.66 | 0.62 | 1.1 | — | — | — |
| Diazinon | 5.12 | 1.16 | 1.06 | 1.1 | 3.11 | 2.84 | 1.1 | — | — | — |
| Malathion | 177.5 | 1.30 | 1.03 | 1.3 | 6.70 | 9.00 | 0.7 | 15.05 | 8.00 | 1.9 |
| Chlorpyrifos | 10.66 | 1.23 | 0.85 | 1.5 | 4.36 | 1.79 | 2.4 | — | — | — |
| Bromophos ethyl | 11.62 | 1.24 | 0.91 | 1.4 | 4.50 | 1.82 | 2.5 | — | — | — |
| Pirimiphos | | | | | | | | | | |

TABLE 6-continued

LD95 values for individual organophosphorus insecticides and compositions of these with permethrin at various ratios against *Musca domestica* (Piggery II strain)

| Compound | LD50 (μg/♀) | Ratio 1:1 | | | Ratio 1:10 (permethrin/OP) | | | Ratio 1:25 (permethrin/OP) | | |
| --- | --- | --- | --- | --- | --- | --- | --- | --- | --- | --- |
| | | Calculated | observed | Calculated observed | Calculated | observed | Calculated observed | Calculated | observed | Calculated observed |
| methyl | 15.6 | 1.26 | 0.91 | 1.4 | 4.92 | 4.28 | 1.5 | 8.15 | 5.02 | 1.6 |

LD50 is the minimum lethal dose expressed in μg required to kill 50% of the flies
OP = organophosphorus compound Factor of potentiation = $\frac{\text{calculated value}}{\text{observed value}}$

What we claim is:

1. An acaricidal composition comprising a pyrethroid of formula

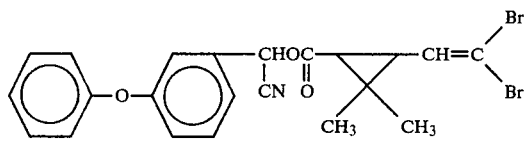

together with at least one acaricidal organophosphorus compound wherein the ratio of said pyrethroid to said organophosphorus compound is in the range of from about 1:1 to 1:20.

2. A composition according to claim 1 wherein the pyrethroid is (—)-α-cyano-3-phenoxybenzyl-(+)-cis-2,2-dimethyl-3-(2,2-dibromovinyl)cyclopropane-1-carboxylate.

3. A composition according to claim 1 wherein the organophosphorus compound is dioxathion.

4. A formulation comprising a composition as defined in claim 1 in admixture with a carrier therefor.

5. A formulation as claimed in claim 4 wherein the organophosphorus compound is selected from the group consisting of coumaphos, bromophos-Ethyl, diazinon, chlorpyrifos, ethion, malathion, oxinothiophos, phosmet, chlorfenvinphos, dioxathion, carbophenothion, crotoxyphos, dicrotophos, benoxaphos and a 1:1 weight by weight mixture of chlorfenvinphos and dioxathion.

6. A formulation as claimed in claim 4 presented as an aqueous suspension, miscible-oil, pressure-pack, wettable dispersible powder, or dusting powder.

7. A formulation as claimed in claim 4 comprising from 0.0001% to 20% weight per volume of the active ingredients.

8. A formulation comprising a composition as defined in claim 1 presented as a diluent free formulation.

9. A method for controlling veterinary ectoparasites of the sub-Orders Ixodoidea or Sarcoptiformes of mammals or birds which comprises the application of a parasiticidally effective amount which is non-toxic to mammals or birds of a composition as defined in claim 1 to the ectoparasite or to its environment.

10. A method according to claim 9 wherein the pyrethroid is (—)-α-cyano-3-phenoxybenzyl-(+)-cis-2,2-dimethyl-3-(2,2-dibromovinyl)cyclopropane-1-carboxylate.

11. A method according to claim 9 wherein the pest is of the sub-Order Ixodoidea.

12. A method according to claim 9 wherein the pest is of the sub-Order Sarcoptiformes.

13. A method according to claim 9 wherein the pest is of the family Ixodidae.

14. A method according to claim 9 wherein the pest is of the genus Rhipicephalus, Amblyomma, Hyalomma, Ixodes, Haemaphysalis, Anocentor, Dermacentor or Boophilus.

15. A method according to claim 9 wherein a formulation comprising said composition in admixture with a carrier is applied.

16. A method according to claim 15 wherein the formulation comprises from 0.0001% to 20% weight by volume of the active ingredients.

17. A method for controlling veterinary ectoparasites of the sub-Orders Ixodoidea or Sarcoptiformes of mammals or birds which comprises the application of a parasiticidally effective amount which is non-toxic to mammals or birds of (A) α-cyano 3-phenoxybenzyl 2,2-dimethyl-3-(2,2 dibromovinyl) cyclopropane-1-carboxylate together with (B) dioxathion wherein the ratio of A:B is in the range of 1:1 to 1:20.

* * * * *